(12) United States Patent
Gerlach

(10) Patent No.: US 7,731,362 B2
(45) Date of Patent: Jun. 8, 2010

(54) OPTICAL SCANNING SYSTEM

(75) Inventor: Mario Gerlach, Aytre (FR)

(73) Assignee: Carl Zeiss Meditec AG, Jena (DE)

( * ) Notice: Subject to any disclaimer, the term of this patent is extended or adjusted under 35 U.S.C. 154(b) by 98 days.

(21) Appl. No.: 11/921,351

(22) PCT Filed: Jul. 22, 2006

(86) PCT No.: PCT/EP2006/007232

§ 371 (c)(1),
(2), (4) Date: Nov. 30, 2007

(87) PCT Pub. No.: WO2007/014661

PCT Pub. Date: Feb. 8, 2007

(65) Prior Publication Data

US 2009/0115967 A1 May 7, 2009

(30) Foreign Application Priority Data

Jul. 30, 2005 (DE) ........................ 10 2005 035 870

(51) Int. Cl.
*A61B 3/10* (2006.01)
(52) U.S. Cl. ..................................... 351/221
(58) Field of Classification Search ................ 351/221, 351/220, 246, 205, 200
See application file for complete search history.

(56) References Cited

U.S. PATENT DOCUMENTS 6,267,477 B1 7/2001 Karpol et al.
6,520,640 B1 * 2/2003 Binnun ........................ 351/206
6,585,723 B1 7/2003 Sumiya
2003/0163122 A1 8/2003 Sumiya

FOREIGN PATENT DOCUMENTS

| | | |
|---|---|---|
| EP | 0 770 370 | 10/1996 |
| EP | 1 192 919 | 10/2001 |
| EP | 1 369 078 | 2/2003 |

* cited by examiner

*Primary Examiner*—Hung X Dang
(74) *Attorney, Agent, or Firm*—Frommer Lawrence & Haug LLP

(57) ABSTRACT

The present application is directed to an optical scanning system for medical applications, preferably in ophthalmology, which can be used for a large range of diagnostic and therapeutic applications. The optical scanning system comprises at least one controllable reflector which has an actuator and which is arranged in a first imaging beam path for deflecting at least one therapy beam and/or diagnosis beam over a work field in a scanning manner, a second imaging beam path for a fixation beam which is imaged on the work field in a spatially fixed manner with respect to the optical axis of the system, and a central control unit. The moving reflector is used to unify the two imaging beam paths and has dichroic characteristics so that it is transmissive for the fixation beam and reflective for the therapy beam and/or diagnosis beam(s). The second radiation source which serves to generate the fixation beam is controlled so as to be synchronized to the position of the moving reflector.

10 Claims, 3 Drawing Sheets

OPTICAL SCANNING SYSTEM

CROSS-REFERENCE TO RELATED APPLICATIONS

This application claims priority of International Application No. PCT/EP2006/007232, filed Jul. 22, 2006 and German Application No. 10 2005 035 870.5, filed Jul. 30, 2005, the complete disclosures of which are hereby incorporated by reference.

BACKGROUND OF THE INVENTION a) Field of the Invention

The present invention is directed to an optical scanning system for medical applications, preferably in ophthalmology. The optical scanning system can be used for a number of diagnostic and therapeutic applications.

b) Description of the Related Art

Applications in the field of diagnostics include retina scanners, OCT systems and systems for mapping the cornea. Retina scanning is an image-generating process for high-resolution representation of the retina for displaying physiology and clinical images. OCT (optical coherence tomography) systems are used for three-dimensional representation of the transparent optical media and make it possible to observe a wide variety of cross sections of the eye, e.g., the cornea, anterior chamber, or eye lens, and in particular also enable an exact measurement of eye length. The measurement principle employed by OCT systems is based on scanning an interferometric beam path over the entire pupil surface for length measurement in transparent media. The spatial structure of the eye can be reproduced from the multitude of local distance data at every location on the pupil. A spatial image of the cornea geometry is determined with topography devices for measuring the cornea in order to prepare for surgical procedures, e.g., LASIK, LASEK, PRK or the like, on the cornea.

However, scanning systems also have therapeutic uses for various eye disorders. The majority of applications are concerned with refractive surgery for correcting defective vision in the human eye. These procedures include, in particular, LASIK, PRK and LASEK. A specific change in the curvature of the cornea is brought about by means of laser radiation to compensate for defective vision of the eye. The procedures mentioned above make use of a therapy laser beam which is guided in a scanning manner over the pupil surface to be corrected.

In most of the optical scanning systems known from the prior art, the visual axis of the eye must be determined and/or maintained. For this purpose, a fixation object is presented to the eye and the patient gazes at this fixation object during the treatment or diagnosis, so that the eye is fixated. An image with a pivot or a small light point can be used as a fixation object. Since the human eye moves the pivot into the center of sharpest vision (fovea), the visual axis of the eye is directed to the optical axis of the external diagnostic or therapeutic system.

FIG. 1 shows by way of example the basic construction of an optical system known from the prior art for scanning the cornea.

The generated measurement beam or therapy beam 1 is deflected corresponding to the desired scan field depending on the quantity of scan directions by at least one moving reflector 2 and strikes a first focusing optical scanner arrangement 3 which generates an intermediate image 4 of the scan field. By means of collimating scanner optics 5, the scan field is imaged to infinity and directed to the objective 7 at a stationary dichroic deflecting mirror 6. This objective 7 serves to focus the measurement beam or therapy beam 1 on the desired imaging plane 8 (in this case, the cornea) in the eye 9. A fixation object 11 is focused on the patient's retina in order to fixate the eye to be examined and/or treated. The fixation object 11 is imaged by imaging optics 13 in the mirror plane of the dichroic deflecting mirror 6 as an intermediate image 12. The intermediate image 12 is imaged to infinity on the cornea by the objective 7 and is focused on the retina 10 through the optical action of the cornea and eye lens.

In contrast to the construction shown in FIG. 1, the fixation object can be coupled into the beam path through an additional dichroic beamsplitter or semitransparent mirror.

In the example shown in the drawing, the intermediate image of the fixation object lies on the surface of the dichroic deflecting mirror. Significant optical imaging errors (astigmatism) which limit the sharpness and point size of the fixation object occur when convergent or divergent beam bundles pass through the medium of the deflecting mirror. Owing to the extensive effect of the imaging errors, it is not possible to generate complicated fixation objects with fine structures on the retina.

The disadvantages of the solutions known from the prior art result from the complexity of the required components. Owing to the combination of the fixation beam path with the measurement beam path and therapy beam path, an intermediate imaging of the scan field is required which substantially increases the quantity of optical components and their requirements for corrective measures. This results in an enormous expenditure on development, manufacture and adjustment.

Another disadvantage which results from the intermediate imaging of the scan field is the unwanted occurrence of non-linear optical effects like random optical breakthrough, phase modulation, or the like. This can lead to reduced reproducibility of the treatment results, particularly for therapy beams with high peak outputs.

OBJECT AND SUMMARY OF THE INVENTION

It is the primary object of the present invention to provide an optical scanning system which achieves a high-quality combination of the fixation beam path, measurement beam path and therapy beam path by overcoming the disadvantages of the prior art. Further, the solution should make it possible to integrate another beam path, particularly for observation and documentation.

According to the invention, the above-stated object is met by an optical scanning system for medical applications including opthalmology comprising at least one controllable reflector which has an actuator which is arranged in a first imaging beam path for deflecting at least one therapy beam and/or diagnosis beam generated by a first radiation source in at least one direction over a work field in a scanning manner; a second imaging beam path for a fixation beam which is generated by a second radiation source and which is imaged on the work field in a spatially fixed manner with respect to the optical axis; and a central control unit, wherein the moving reflector is used to unify the two imaging beam paths for the fixation beam and the therapy beam and/or diagnosis beam(s). The moving reflector has dichroic characteristics so that the reflector is transmissive for the fixation beam and reflective for the therapy beam and/or diagnosis beam(s). The second radiation source which serves to generate the fixation beam is controlled so as to be synchronized to the position of the moving reflector.

Although the present invention is provided as an optical scanning system preferably for diagnostic and therapeutic applications in the field of ophthalmology, it can also be applied to other areas of medicine such as, for example, dermatological treatment.

The invention will be described more fully in the following with reference to embodiment examples.

BRIEF DESCRIPTION OF THE PREFERRED EMBODIMENTS

The optical scanning system according to the invention for medical applications, preferably in ophthalmology, comprises at least one controllable reflector which has an actuator and which is arranged in a first imaging beam path for deflecting at least one therapy beam and/or diagnosis beam generated by a first radiation source in at least one direction over a work field in a scanning manner, a second imaging beam path for a fixation beam path which proceeds from a second radiation source and which is imaged in a spatially fixed manner in the work field, and a central control unit.

According to the invention, the moving reflector is used to unify the two beam paths for imaging the fixation object and the therapy beam and/or diagnosis beam(s). The moving reflector has dichroic characteristics so that the optical element is transmissive for the fixation beam bundle and reflective for the therapy beam and/or diagnosis beam. The second radiation source which serves to generate the fixation beam bundle is controlled by the central control unit so as to be synchronized to the position of the moving reflector.

Two moving, controllable reflectors having actuators are arranged in the first imaging beam path in order to deflect the therapy beam and/or diagnosis beam generated by the first radiation source in two directions over the work field in a scanning manner. The optical incident plane and deflection plane of the two reflectors are preferably arranged at 90° relative to one another. But for the sake of simplicity the following description is limited to solutions with only one moving reflector.

In an advantageous construction, the optical scanning system has additional means for correcting astigmatism and for dioptric compensation.

While the first radiation source for generating the therapy beam and/or diagnosis beam(s) is preferably a laser source, a self-luminous illumination element is preferably used for the second radiation source for generating different fixation objects. However, it is also possible to arrange an additional non-self-luminous optical element in front of the second radiation source for generating different fixation objects.

Figure 1:
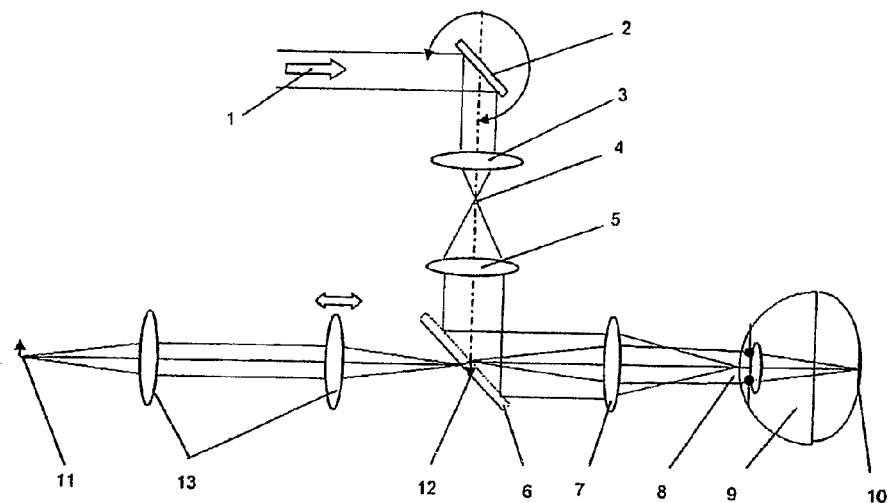
FIG. 1, as mentioned above, shows a prior example of an optical system for scanning the cornea.
Figure 2:
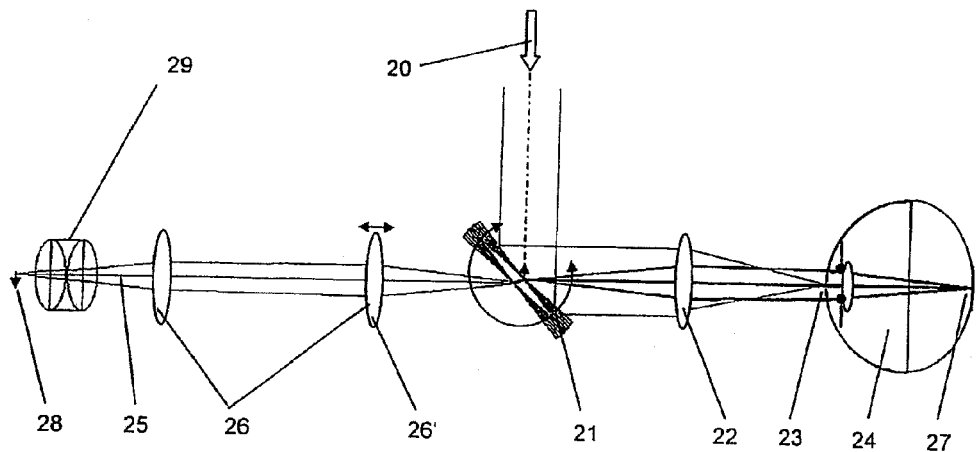
FIG. 2 shows a basic view of the optical scanning system with two illumination beam paths.

For purposes of a clearer illustration, FIG. 2 shows a basic view of the optical scanning system with two imaging beam paths. The therapy beam and/or diagnosis beam 20 are/is deflected from the first radiation source, not shown, to a moving, controllable reflector 21 and focused by an objective 22 in the front portion 23 of the eye 24. The reflector 21 serves to deflect the therapy beam and/or diagnosis beam 20 in a scanning manner in one direction over a work field and has an actuator. The reflector 21 preferably swings and/or oscillates around a central position.

Proceeding from the second radiation source, not shown, the fixation beam bundle 25 is imaged to infinity by imaging optics 26, the reflector 21 and one objective 22 in a spatially fixed manner and parallel to the optical axis of the system and is subsequently focused on the retina 27 of the eye 24 by the front portion 23 of the eye comprising the cornea, intraocular fluid, and eye lens.

The two imaging beam paths are unified by means of the reflector 21 which has dichroic characteristics so that it is transmissive for the fixation beam bundle 25 and reflective for the therapy beam and/or diagnosis beam 20.

The second radiation source which generates the fixation beam bundle 25 is controlled by the central control unit, not shown, so as to be synchronized to the position of the reflector 21 in that it is periodically switched on for a certain period of time when the same position of the reflector 21 is reached, a stroboscopic fixation object 28 being generated in this way. The fixation object 28 itself can be generated directly by a self-luminous illumination element such as individual LEDs or laser diodes, LED arrays, or laser diode arrays, LCD, TFT, or the like.

However, it is also possible to use non-self-luminous elements and/or structures for generating different fixation objects 28 which are preferably illuminated by one or more LEDs, laser diodes or strobe lamps.

An intermediate image of the fixation object 28 is generated at the center of rotation of the reflector 21 by means of the imaging optics 26. Additional means are provided in the second illumination beam path for dioptric compensation of eyes with defective vision. For this purpose, the imaging optics 26 have a displaceable optical element 26'.

Similar to the prior art solution described above, optical imaging errors, particularly astigmatism, occur when convergent or divergent beam bundles pass through an inclined plane plate. This is characterized by an inequality of the radii of curvature of the wave fronts behind the plane plate in two directions orthogonal to one another, so that astigmatic beam bundles have different focus positions in the respective propagation direction after focusing with spherical optics.

Optical elements which are not axially symmetric, e.g., cylindrical optics or the like, can be used to correct this astigmatism. But it is also possible to correct the occurring astigmatism by means of a compensating plate 29 whose incident plane is rotated preferably by 90° around the optical axis relative to the incident plane of the reflector 21. For this purpose, the compensating plate 29 is arranged in the vicinity of the first illumination source. The angle of inclination of the compensating plate 29 depends on the latter's respective thickness and refractive index as well as on the optical characteristics (thickness and refractive index) of the reflector 21 which is used. The compensating plate 29 is dimensioned in such a way that the astigmatic imaging error of the optical scanning system is corrected in the neutral position of the reflector 21.

Owing to this compensation for astigmatism, more finely structured fixation objects 28 can be imaged on the retina 27 of the eye 24, the pivots of these fixation objects 28 holding the gaze of the eye during the treatment period.

A second set of problems arises from the fact that a lateral offset of the beam occurs when optical radiation passes through inclined plane plates. The extent of the offset depends on the geometric characteristics (thickness, angle of incidence) and optical characteristics (refractive index) of the plane plate. Since the dependence of the occurring offset on the angle of incidence is nonlinear, a simple compensation is possible only when the angle of incidence is constant. If the offset is not compensated, there is a blurring of the image of the fixation object 28 parallel to the incident plane of the reflector 21 due to the fast rotating and tilting movement of the reflector 21.

To correct this blurring of the image of the fixation object 28, the second illumination source for generating the fixation beam 25 synchronous to the position of the reflector 21 is controlled by the central control unit in that it is periodically switched on for a certain period of time when the same position of the reflector 21 is reached, a stroboscopic fixation object 28 being generated in this way.

Figure 3:
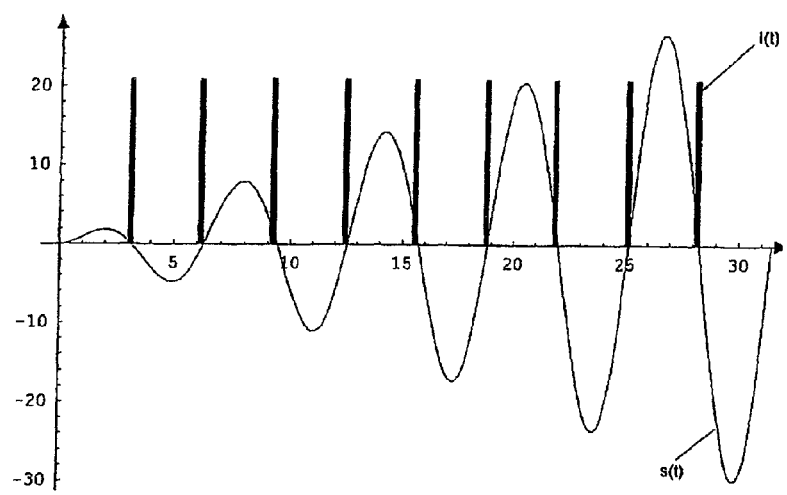
FIG. 3 shows control signals for the second illumination source in relation to the movement of the reflector.

FIG. 3 shows the control signals for the second radiation source in relation to the movement of the reflector 21. The movement path s(t) of the reflector 21 and the times of the control pulses I(t) for the second radiation source which are derived from this movement path s(t) are shown by way of example. The angle of rotation of the actuator connected to the reflector 21 changes in proportion to the applied control voltage. For application in scanning systems, the reflector 21 preferably oscillates around a defined center position.

This center position is characterized, for example, by a zero crossover of the control voltage. When no continuous illumination is used but, instead, the illumination voltage is triggered at this zero crossover, the retina 27 of the eye 24 can be focused on by an induced stroboscopic effect of the fixation object 28 without imaging errors. The shorter the illumination period, the smaller the imaging errors. The illumination period is oriented to the required image quality of the fixation object 28.

The length of the illumination pulses depends on the respective speed of the reflector 21 at the zero crossover and is permanently adapted directly by the central control unit. Since the frequency of the reflector 21 is appreciably higher than the frequency that can be registered by the human eye, the patient perceives an apparently continuously luminous fixation object 28.

However, it is also possible to generate the trigger signals for the second radiation source with maximum elongation, which offers the advantage of the lowest mirror speed. Therefore, the active illumination pulse duration can last appreciably longer.

In another advantageous construction, the second radiation source for generating the fixation beam is controlled in such a way that the radiation source is only triggered every nth time that the same position of the moving reflector 21 is reached for a determined number of cycles, and a stroboscopic fixation object 28 with a lower modulation frequency is accordingly generated. This has the advantage that the low-frequency visible modulation of the fixation object 28 leads to an improvement in the attentiveness of the patient.

Aside from the unification of the two illumination beam paths for the fixation beam and the therapy beam and/or diagnosis beam, another optical beam path can also be added. This optical beam path is preferably used for observation and/or documentation.

Figure 4:
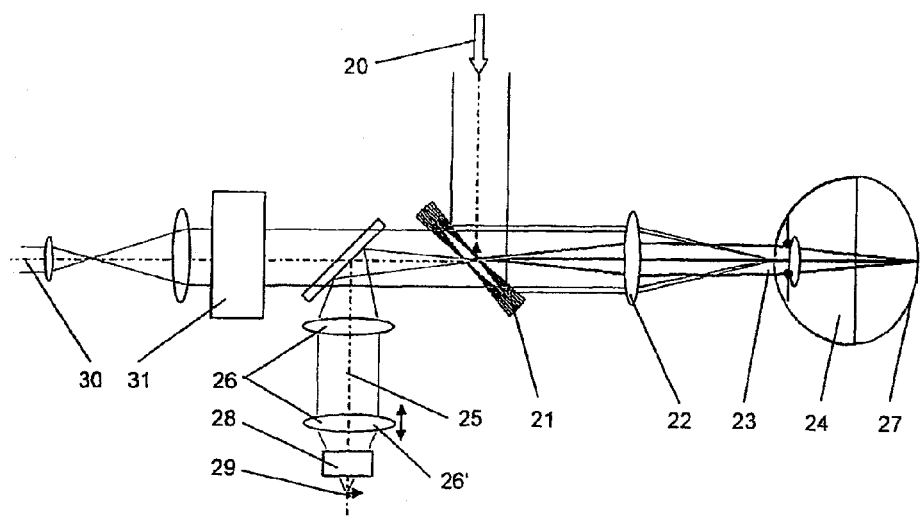
FIG. 4 shows a first optical scanning system with two illumination beam paths and an observation beam path.

FIG. 4 shows a first optical scanning system with a therapy beam path and/or diagnosis beam path, a fixation beam path, and an additional observation beam path.

In the optical scanning system, another optical beam path for observation and/or documentation is likewise combined with the two imaging beam paths for the fixation beam 25 and the therapy beam and/or diagnosis beam(s) 20 by the moving reflector 21.

If observation is to take place during the scanning process, it is necessary to provide a fast optical switch 30 for blocking and releasing the beam path for observation and/or documentation. The blocking and releasing is likewise controlled depending on the position of the controllable reflector 21.

In this connection, LCD modulators, EO modulators, MEMS, DMD, or the like, which deliberately interrupt the beam path for observation and/or documentation during the cycling of the mirror are preferably used as an optical switch 30.

As with the triggered illumination voltage of the second illumination source described above, the triggering time can be set at the zero crossover of the movement path s(t) of the reflector 21 or its maximum value.

Figure 5:
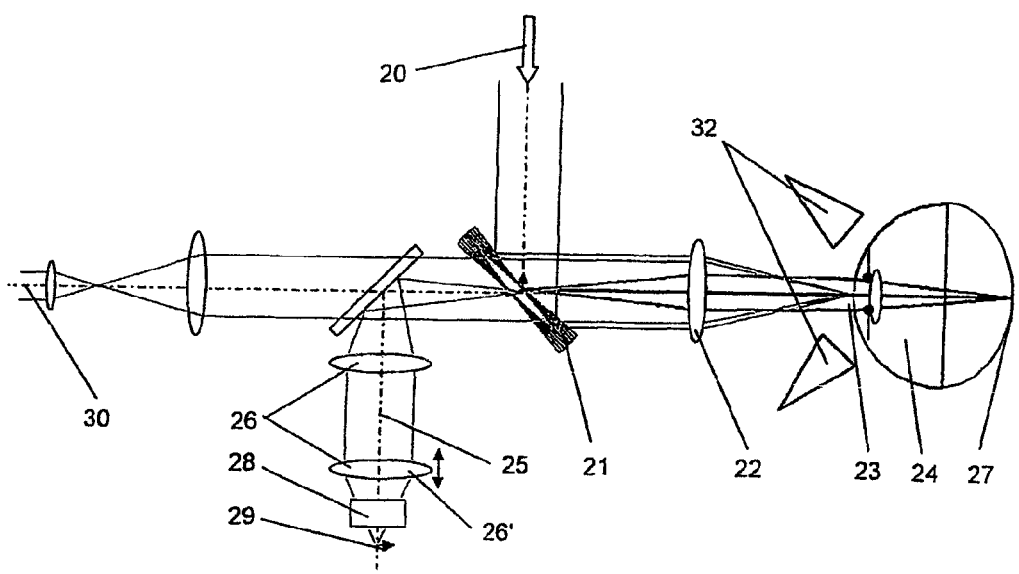
FIG. 5 shows a second optical scanning system with two illumination beam paths and an observation beam path.

FIG. 5 shows a second optical scanning system with two imaging beam paths and an observation beam path.

The optical switch 30 arranged in the unified beam path of the optical scanning system according to FIG. 4 can be omitted when an additional, third radiation source 31 for the discontinuous stroboscopic illumination of the work field is provided outside the unified beam path. The control of its illumination intervals is also carried out in this case as a function of the position of the controllable reflector 21.

A very brief illumination period leads to an observation image which is free of distortion. Similarly, the triggering time can advantageously be set at the zero crossover of the movement path s(t) of the reflector 21 or its maximum value.

Radiation sources which can change their illumination intensity within short time intervals, e.g., laser diodes, LEDs or strobe lamps, are preferably used. Continuous illumination sources can be used when a fast optical switch which modulates the illumination intensity in the described manner is provided between the radiation source and the work field.

The arrangement according to the invention offers an optical scanning system for medical applications, preferably for ophthalmology, which has a substantially simplified optical construction due to the dual function of the moving scanning reflector. The proposed solution makes it possible to unify three or more optical beam paths in a very small space.

Substantial savings in development, manufacture and adjustment are achieved by reducing the quantity of required optical components. In an advantageous manner, the proposed technical solution enables a correction of astigmatism and a dioptric compensation of the fixation beam path for vision-impaired eyes.

In addition, the construction of the optical scanning system according to the invention makes it possible to use lasers with very high pulse peak outputs because no focusing intermediate imaging is used in which a random optical breakthrough can occur. Accordingly, a substantially improved image quality can be achieved compared to the solutions known from the prior art.

While the foregoing description and drawings represent the present invention, it will be obvious to those skilled in the art that various changes may be made therein without departing from the true spirit and scope of the present invention.

What is claimed is:

1. An optical scanning system for medical applications, including ophthalmology, comprising:
    at least one controllable reflector which has an actuator and which is arranged in a first imaging beam path for deflecting at least one therapy beam and/or diagnosis beam generated by a first radiation source in at least one direction over a work field in a scanning manner;
    a second imaging beam path for a fixation beam which is generated by a second radiation source and which is imaged on the work field in a spatially fixed manner with respect to the optical axis; and a central control unit;
wherein the moving reflector is used to unify the two imaging beam paths for the fixation beam and the therapy beam and/or diagnosis beam, said moving reflector having dichroic characteristics so that the reflector is transmissive for the fixation beam and reflective for the therapy beam and/or diagnosis beam; and
wherein said second radiation source which serves to generate the fixation beam is controlled so as to be synchronized to the position of the moving reflector.

2. The optical scanning system according to claim 1;
wherein at least two controllable reflectors having actuators are arranged in the first imaging beam path in order that at least one therapy beam and/or diagnosis beam generated by a first radiation source is deflected in two directions over the work field in a scanning manner.

3. The optical scanning system according to claim 1;
wherein additional means are provided for correcting astigmatism and for dioptric compensation.

4. The optical scanning system according to claim 1;
wherein the first radiation source for generating the therapy beam and/or diagnosis beam(s) is a laser source.

5. The optical scanning system according to claim 1;
wherein the second radiation source is constructed as a self-luminous illumination element for generating different fixation objects, or non-self-luminous optical elements are arranged for generating different fixation objects and are illuminated by the second radiation source.

6. The optical scanning system according to claim 1;
wherein the second radiation source for generating the fixation beam is controlled in such a way that it is periodically switched on for a certain period of time when the same position of the moving reflector is reached, a stroboscopic fixation object being generated in this way.

7. The optical scanning system according to claim 1;
wherein the second radiation source serving to generate the fixation beam is controlled in such a way that it is periodically switched on for a certain number of cycles when the same position of the moving reflector is reached for the nth time, a stroboscopic fixation object with visible modulation frequency being generated in this way.

8. The optical scanning system according to claim 1;
wherein the fixation object is focused at the center of rotation of the moving dichroic reflector element.

9. The optical scanning system according to claim 1;
wherein at least one additional optical beam path for observation and/or documentation is provided and is unified with the two imaging beam paths for the fixation beam and the therapy beam and/or diagnosis beam(s), and wherein an optical switch is arranged in the unified beam path for blocking and releasing the beam path for observation and/or documentation, wherein the blocking and releasing is controlled depending on the position of the controllable reflector.

10. The optical scanning system according to claim 1;
wherein the optical switch arranged in the unified beam path for blocking and releasing the beam path for observation and/or documentation can be omitted when an additional, third radiation source for the discontinuous illumination of the work field is provided outside the unified beam path, wherein its illumination intervals are controlled depending on the position of the controllable reflector.

* * * * *